(12) United States Patent
Nishimura et al.

(10) Patent No.: US 6,179,967 B1
(45) Date of Patent: Jan. 30, 2001

(54) PURIFICATION PROCESS OF PENTAFLUOROETHANE

(75) Inventors: Atsuo Nishimura; Reiji Takahashi, both of Kanagawa (JP)

(73) Assignee: Showa Denko K.K., Tokyo (JP)

( * ) Notice: Under 35 U.S.C. 154(b), the term of this patent shall be extended for 0 days.

(21) Appl. No.: 08/248,728

(22) Filed: May 25, 1994

(30) Foreign Application Priority Data

May 25, 1993 (JP) ..................................... 5-122869

(51) Int. Cl.$^7$ ....................................... B01D 3/34
(52) U.S. Cl. ................. 203/60; 203/62; 203/63; 203/70; 570/178
(58) Field of Search ................. 203/62, 63, 60, 203/70; 570/178

(56) References Cited

U.S. PATENT DOCUMENTS

| | | |
|---|---|---|
| 2,442,589 | 6/1948 | Evans et al. |
| 3,101,304 * | 8/1963 | Wiist ..................................... 203/67 |
| 3,282,801 * | 11/1966 | Wiist ..................................... 203/63 |
| 5,087,329 * | 2/1992 | Felix ..................................... 203/67 |
| 5,346,595 * | 9/1994 | Clemmer et al. ..................... 203/75 |

FOREIGN PATENT DOCUMENTS

| | | | |
|---|---|---|---|
| 574756A1 * | 12/1993 | (EP) | ..................................... 570/178 |
| 471760 | 4/1969 | (SE) . | |
| WO93/23355 * | 5/1993 | (WO) | ..................................... 570/178 |

* cited by examiner

Primary Examiner—Robert J. Warden, Sr.
(74) Attorney, Agent, or Firm—Sughrue, Mion, Zinn, Macpeak & Seas, PLLC

(57) ABSTRACT

A purification process of pentafluoroethane from a crude pentafluoroethane containing chloropentafluoroethane as a by-product by extractive distillation using an extracting reagent having a standard boiling point of from −10° C. to 100° C. and being selected from paraffinic hydrocarbons, alcohols, ethers, esters, and ketones.

3 Claims, No Drawings

PURIFICATION PROCESS OF PENTRAFLUOROETHANE

FIELD OF THE INVENTION

The present invention relates to a purification process of pentafluoroethane, and more specifically to a purification process of pentafluoroethane by an extractive distillation method using an extracting reagent.

BACKGROUND OF THE INVENTION

Monoclorodifluoromethane (hereinafter referred to as HCFC-22) which has hitherto been widely used as a refrigerant, etc., for an air conditioner, refrigerator, etc., becomes an object of the world-wide regulation as a material of destroying the ozone layer existing in the stratosphere, that is, as a regulated fluorinated hydrocarbon. Thus, pentafluoroethane (hereinafter referred to as HFC-125) having the similar properties as HCFC-22 has been watched with interest as one of substitutes for HCFC-22.

Since HFC-125 is usually produced by reacting perchloro ethane and hydrogen fluoride as raw materials, monochloropentanfluoroethane (hereinafter referred to as CFC-115) is frequently contained in the product as a by-product. However, CFC-115 is also is an object of the world-wide regulation as a controlled fluorinated hydrocarbon (CFC) and must be separated.

As one of methods of separating a fluid mixture into constituting components, a distillation method is the most general method. According to the inventors' investigations, however, the relative volatility of a little amount of CFC-115 to HFC-125 is near 1, for example, the relative volatility is from 1.01 to 1.02, under the pressure of near 5 kg/cm² G, and hence it is very difficult to separate HFC-125 from CFC-115 by a simple distillation method.

Under the circumstance, an extractive distillation method of performing a distillation by adding to a fluid mixture, as an extracting reagent, a compound having a different boiling point than the constituting components of the fluid mixture is applied. For example, U.S. Pat. No. 5,082,329 discloses a process of separating HFC-125 from a crude HFC-125 containing CFC-115 by carrying out an extractive distillation using a controlled CFC as an extracting reagent. The extracting reagent is exemplified with 1,2-dichlorotetrafluoroethane, etc. and the extracting reagent itself is a controlled CFC.

SUMMARY OF THE INVENTION

An object of the present invention is, therefore, to provide a process of purifying HFC-125, without using such a controlled CFC as an extracting reagent, by extractive distillation of a crude HFC-125 to separate HFC-125 from by-product CFC-115.

As a result of various investigations, it has been found that the above-described object can be achieved by extractive distillation of a crude HFC-125 containing CFC-115 using an extracting reagent having a standard boiling point (i.e., a boiling point under atmospheric pressure) in the range of from –10° C. to 100° C. and being selected from paraffinic hydrocarbons, alcohols, ethers, esters, and ketones.

DETAILED DESCRIPTION OF THE INVENTION

In the present invention, the above-described extracting reagent increases or decreases the relative volatility of CFC-115 to HFC-125 to be apart from 1, whereby the separation of the components becomes possible.

The relative volatility is well known and is defined as a ratio of the equilibrium constants of the constituting components of a fluid mixture. In the case where the constituting components are HFC-125 and CFC-115, the relative volatility of CFC-115 to HFC-125 is shown by the following formula (1).

$$(A)=(B)/(C)=[(D)/(E)]/[(F)/(G)] \quad (1)$$

(A): Relative volatility of CFC-115 to HFC-125
(B): Equilibrium constant of CFC-115
(C): Equilibrium constant of HFC-125
(D): Mole fraction of CFC-115 in vapor phase
(E): Mole fraction of CFC-115 in liquid phase
(F): Mole fraction of HFC-125 in vapor phase
(G): Mole fraction of HFC-125 in liquid phase As is clear from the above formula, if the relative volatility of CFC-115 to HFC-125 is 1, the compositions of both the vapor and liquid phases become same and the separation by distillation becomes impossible. When the relative volatility is larger than 1, the mole fraction of CFC-115 of the vapor phase becomes larger than the mole fraction of CFC-115 of liquid phase and since CFC-115 is concentrated in the vapor phase, the speparation by distillation becomes possible. When the relative volatility is less than 1, the mole fraction of CFC-115 of a liquid phase become larger than the mole fraction of CFC-115 in vapor phase and since CFC-115 is concentrated to the liquid phase, the separation by distillation becomes possible.

The extracting reagent for practical use is required to have the following properties.

(1) the selectivity is high,
(2) the solubility is high,
(3) the standard boiling point is in a proper range,
(4) the recovery of the extracting reagent is easy, that is, the difference in boiling point from those of HFC-125 and CFC-115 is large, and
(5) the extrcting reagent does not react with HFC-125 and CFC-115.

When a value of the relative volality in the presence of an extracting reagent devided by the relative volatility in the absence of an extracting reagent is larger than 1 or less than 1, it can be said that such a extracting reagent has a high selectivity.

Taking account of easiness of the separation of the extracting reagent from HFC-125 and CFC-115 by distillation, the standard boiling point of the extracting reagent is necessarily higher than the standard boiling points of HFC-125 and CFC-115 to some extent. Practically, it is preferred that the difference in boiling point between HFC-125 or CFC-115 and the extracting reagent is at least about 30° C., and more preferably about 40° C. or more. Since the boiling points of HFC-125 and CFC-115 are –48.5° C. and –38.7° C., respectively, the extracting reagent preferrably has a standard boiling point of at least –10° C. However, the boiling point should not be too high so that a specific heating source is not needed and the temperature distribution in a distillation column for separation of the extracting reagent can be moderated. Practically, it is preferred that the difference in boiling point between HFC-125 or CFC-115 to be separated and the extracting reagent is not more than about 140° C., and more preferably not more than 120° C. Hence, it is preferred to select an extracting reagent having a standard boiling point of not higher than 100° C.

In addition, as the result of investigating the solubility and the reactivity to HFC-125 and CFC-115, it has been found that paraffinic hydrocarbons, alcohols, ethers, esters, and ketones each having a standard boiling point of from −10° C. 100° C. are preferred as the extracting reagent.

In the measurement of the relative volatility described above, a crude HFC-125 containing about 3 mole % CFC-115 was charged in the Osmer vapor-liquid equilibrium apparatus made of stainless steel, and each of various extracting reagent was added thereto. After the liquid/vapor system reached to an equilibrium state at a constant temperature of 20° C., the liquid phase and the vapor phase were sampled. The composition of each phase was analyzed by gas chromatography, and the relative volatility was determined by formula (1) described above based on the analytical value.

The relative volatilities of CFC-115 to HFC-125 with various extrcting reagents as measured above are shown in Table 1 below.

TABLE 1

| Extracting reagent | Concentration of Extracting Reagent in Liquid Phase | Relative Volatility of CFC-115 to HFC-125 |
|---|---|---|
| Paraffinic hydrocarbons | | |
| n-Pentane (36)* | 80 | 0.4 |
| i-Pentane (28) | 74 | 0.5 |
| n-Hexane (69) | 79 | 0.6 |
| Alcohols | | |
| Methyl alcohol (65) | 81 | 4.5 |
| n-Propyl alcohol (97) | 78 | 2.1 |
| i-Propyl alcohol (82) | 84 | 2.7 |
| Ethyl alcohol (78) | 79 | 1.9 |
| Ethers | | |
| Diethyl ether (35) | 58 | 1.7 |
| Esters | | |
| Ethyl formate (54) | 82 | 4.5 |
| Methyl acetate (57) | 81 | 4.7 |
| Ethyl acetate (77) | 70 | 2.3 |
| Ketones | | |
| Acetone (56) | 81 | 6.4 |
| Ethyl methyl ketone (79) | 65 | 3.2 |

Note: *Standard boiling point (° C.) in parentheses

As is seen from the results shown in Table 1, when the extractive distillation is carried out using the paraffinic hydrocabon having a standard boiling point in the range of from −10° C. to 100° C. as an extracting reagent, the relative volatility of CFC-115 to HFC-125 is reduced below 0.6, and in particular, when n-pentane is used as an extracting reagent, the relative volatility is reduced to 0.4. Thus, by carrying out the extractive distillation using a paraffinic hydrocarbon having a standard boiling point in the range of from −10° C. to 100° C., CFC-115 can be separated from HFC-125 as a high-boiling component.

It has also found that when the extractive distillation is carried out using an alcohol having a standard boiling point in the range of from −10° C. to 100° C. as an extracting reagent, the relative volatility of CFC-115 to HFC-125 is increased to more than 1.9 and, in particular, in the case of using methyl alcohol as an extracting reagent, the relative volatility is increased to 4.5. Thus, by carrying out the extractive distillation using an alcohol having a standard boiling point in the range of from −10° C. to 100° C. as an extracting reagent, CFC-115 can be separated from HFC-125 as a low-boiling component.

It has further been found that when the extractive distillation is carried out using an ether having a standard boiling point in the range of from −10° C. to 100° C. as an extracting reagent, the relative volatility of CFC-115 to HFC-125 is increased at least 1.7. In particular, diethyl ether is suitable. Thus, by carring out the extractive distillation using an ether having a standard boiling point in the range of from −10° C. to 100° C. as an extracting reagent, CFC-115 can be separated from HFC-125 as a low-boiling component.

It has also been found that when the extractive distillation is carried out using an ester having a standard boiling point in the range of from −10° C. to 100° C. as an extracting reagent, the relative volativity of CFC-115 to HFC-125 is increased at least 2.3 and in particular, when methyl acetate is used as an extracting reagent, the relative volatility is increased to 4.7. Thus, by carrying out the extractive distillation using an ester having a standard boiling point in the range of from −10° C. to 100° C., CFC-115 can be separated from HFC-125 as a low-boiling component.

Furthermore, it has been found that when the extractive distillation is carried out using a ketone having a standard boiling point in the range of from −10° C. to 100° C. as an extracting reagent, the relative volatility of CFC-115 to HFC-125 is increased at least 3.5 and in particular, when acetone is used as an exracting reagent, the relative volativity is increased to 6.4. Thus, by carrying out the extractive distillation using a ketone having a standard boiling point in the range of from −10° C. to 100° C. as an extracting reagent, CFC-115 can be separated from HFC-125 as a low-boiling component.

As described above, by the use of the extracting reagent of the present invention, the relative volatility of CFC-115 to HFC-125 can be reduced to below 1, and preferably below 0.6 or the relative volativity can be increased to more than 1, and preferably at least 1.7, whereby HFC-125 and CFC-115 are separated from each other by extractive distillation and HFC-125 can be obtained at a high purity.

Of the foregoing extracting reagents, particularly preferred are n-pentane and acetone.

In general, as the concentration of the extracting reagent increases, it is more advantageous to make the relative volativity apart from 1. In the case of using acetone, for example, the concentration is generally 30% by weight or higher, and preferably in the range of from 50% by weight to 90% by weight.

The foregoing extracting reagents may be used singly or as a mixture thereof. In the case of using them as a mixrure, it is possible to use those reducing the relative volatility of CFC-115 to HFC-125 to below 1 in combination, or to use those increasing the relative volatility to more than 1 in combination. However, it is not preferred to use an extracting reagent of reducing the relative volatility to below 1 and an extracting reagent of increasing the relative volatility to more than 1 in combination.

By carrying out the extractive dsitillation using the paraffinic hydrocaron capable of reducing the relative volatility of CFC-115 to HFC-125 below 1 as the extracting reagent, almost all CFC-115 contained in a crude HFC-125 can be discharged from the bottom portion of the extractive distilling column together with the extracting reagent and highly pure HFC-125 is obtained as a distillate.

When the extractive distillation is carried out using an extracting reagent capable of increasing the relative volatility to more than 1, such as an alcohol, an ether, an ester, or an ketone, almost all CFC-115 contained in a crude HFC-125 can be discharged as a distillate from the extractive distilling column and HFC-125 containing almost no CFC-115 is obtained from the bottom together with the extracting reagent.

Then, the present invention is described more practically by the following examples.

EXAMPLE 1

In stainless steel rectifying column having a diameter of 4 cm and a theoretical stage number of 20 stages, a crude HFC-125 containing 2.9 mole % of CFC-115 was supplied to the rectifying column at a position of the 13th stage from the top of the column at a pressure of 5.9 Kg/cm$^2$ G and a rate of 0.29 Kg/hour, and acetone was supplied to the column at a position of the 3rd stage from the top of the column at a rate of 2.00 Kg/hour. A distillate was obtained from the top of the column at a reflux ratio of 30 and a rate of 0.05 Kg/hour. The results are shown in Table 2 below.

The bottom product was re-distilled to completely separate acetone, whereby HFC-125 having a purity of 99.95% (containing 0.05% of CFC-115) was obtained.

TABLE 2

|  | Supply of Crude HFC-125 | Supply of Extracting Reagent | Distillate | Bottom Product |
|---|---|---|---|---|
| Flow Rate (kg/h) | 0.29 | 2.00 | 0.05 | 2.24 |
| Composition (mol %) |  |  |  |  |
| HFC-125 | 97.1 | — | 63.43 | 11.154 |
| CFC-115 | 2.9 | — | 16.57 | 0.006 |
| Acetone | — | 100 | 20 | 88.84 |

EXAMPLE 2

In a stainless steel rectifying column having a diameter of 4 cm and a theoretical stage number of 40 stages, a crude HFC-125 containing 2.9 mole % of CFC-115 was supplied at a position of the 30th stage from the top of the column at a pressure of 5.9 Kg/cm$^2$ G and a rate of 0.4 Kg/hour, and n-pentane was supplied at a position of the 10th stage from the top of the column at a rate of 2.00 Kg/hour. A distillate was obtained from the top of the tower at a reflux ratio of 5 and a rate of 0.32 Kg/hour. The results are shown in Table 3 below. HFC-125 having a purity of 99.93% (containing 0.07% of CFC-115) was obtained as the distillate.

TABLE 3

|  | Supply of Crude HFC-125 | Supply of Extracting Reagent | Distillate | Bottom Product |
|---|---|---|---|---|
| Flow Rate (kg/h) | 0.40 | 2.00 | 0.32 | 2.08 |
| Composition (mol %) |  |  |  |  |
| HFC-125 | 97.1 | — | 99.93 | 2.77 |
| CFC-115 | 2.9 | — | 0.07 | 0.46 |
| n-Pentane | — | 100 | — | 96.77 |

As described above, the purification process of HFC-125 according to the present invention is an excellent process capable of easily removing CFC-115 from HFC-125, the separation of which has hitherto been difficult by conventional processes.

While the invention has been described in detail and with reference to specific embodiments thereof, it will be apparent to one skilled in the art that various changes and modifications can be made therein without departing from the spirit and scope thereof.

What is claimed is:

1. A purification process of pentafluoroethane, which comprises removing chloropentafluoroethane contained as an impurity in pentafluoroethane by extractive distillation using an extracting reagent having a standard boiling point of from −10° C. to 100° C., wherein the extracting reagent is selected from the group consisting of paraffinic hydrocarbons, alcohols, ethers, esters, and ketones.

2. The purification process as in claim 1, wherein said extracting reagent is selected from the group consisting of n-pentane, i-pentane, n-hexane, methyl alcohol, isopropyl alcohol, ethyl alcohol, ethyl formate, methyl acetate, ethyl acetate, acetone, and methyl ethyl ketone.

3. The purification process as in claim 2, wherein said extracting reagent is n-pentane or acetone.

* * * * *